(12) United States Patent
Van Westrenen

(10) Patent No.: US 8,987,540 B2
(45) Date of Patent: *Mar. 24, 2015

(54) PROCESS FOR REMOVING OXYGENATE FROM AN OLEFIN STREAM

(71) Applicant: Shell Oil Company, Houston, TX (US)

(72) Inventor: Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/136,150

(22) Filed: Dec. 20, 2013

(65) Prior Publication Data

US 2014/0187804 A1    Jul. 3, 2014

(30) Foreign Application Priority Data

Dec. 28, 2012  (EP) .................................. 12199686

(51) Int. Cl.
| | | |
|---|---|---|
| C07C 7/00 | (2006.01) | |
| C07C 7/10 | (2006.01) | |
| C07D 301/03 | (2006.01) | |
| C07C 1/20 | (2006.01) | |
| C07C 7/08 | (2006.01) | |

(52) U.S. Cl.
CPC ............... *C07C 7/10* (2013.01); *C07D 301/03* (2013.01); *C07C 1/20* (2013.01); *C07C 7/08* (2013.01)
USPC .......................................... 585/864; 585/329

(58) Field of Classification Search
CPC ............ C07C 1/20; C07C 7/08; C07C 11/04; C07C 11/06; C07D 301/03
USPC .......................... 549/523; 585/324, 329, 864
See application file for complete search history.

(56) References Cited

U.S. PATENT DOCUMENTS

| | | | |
|---|---|---|---|
| 4,567,029 A | 1/1986 | Wilson et al. | |
| 7,002,050 B2 | 2/2006 | Santiago Fernandez et al. | |
| 7,132,580 B1 | 11/2006 | Senetar | |
| 2003/0045655 A1 | 3/2003 | Hendriksen et al. | |
| 2007/0155999 A1 | 7/2007 | Pujado et al. | |
| 2007/0203380 A1 | 8/2007 | Vora et al. | |
| 2009/0223870 A1 | 9/2009 | Birke et al. | |
| 2014/0171665 A1* | 6/2014 | Van Westrenen | ............. 549/524 |

FOREIGN PATENT DOCUMENTS

| | | |
|---|---|---|
| WO | 03020678 | 3/2003 |
| WO | 2006020083 | 2/2006 |

OTHER PUBLICATIONS

Nowowiejski et al., An overview of oxygenates in olefins units in relation to corrosion, fouling product specifications, and safety, Presentation at American Institute of Chemical Engineers 2003 Spring National Meeting, New Orelans, USA, in particular p. 16.

* cited by examiner

*Primary Examiner* — T. Victor Oh

(57) ABSTRACT

The present invention relates to a process for removing oxygenate from an olefin stream comprising oxygenate, comprising providing to an oxygenate recovery zone the olefin stream comprising oxygenate and a solvent comprising propanol, treating the olefin stream comprising oxygenate with the solvent, and retrieving from the oxygenate recovery zone at least one oxygenate-depleted olefinic product stream comprising olefin and a spent solvent comprising at least part of the oxygenate.

8 Claims, 1 Drawing Sheet

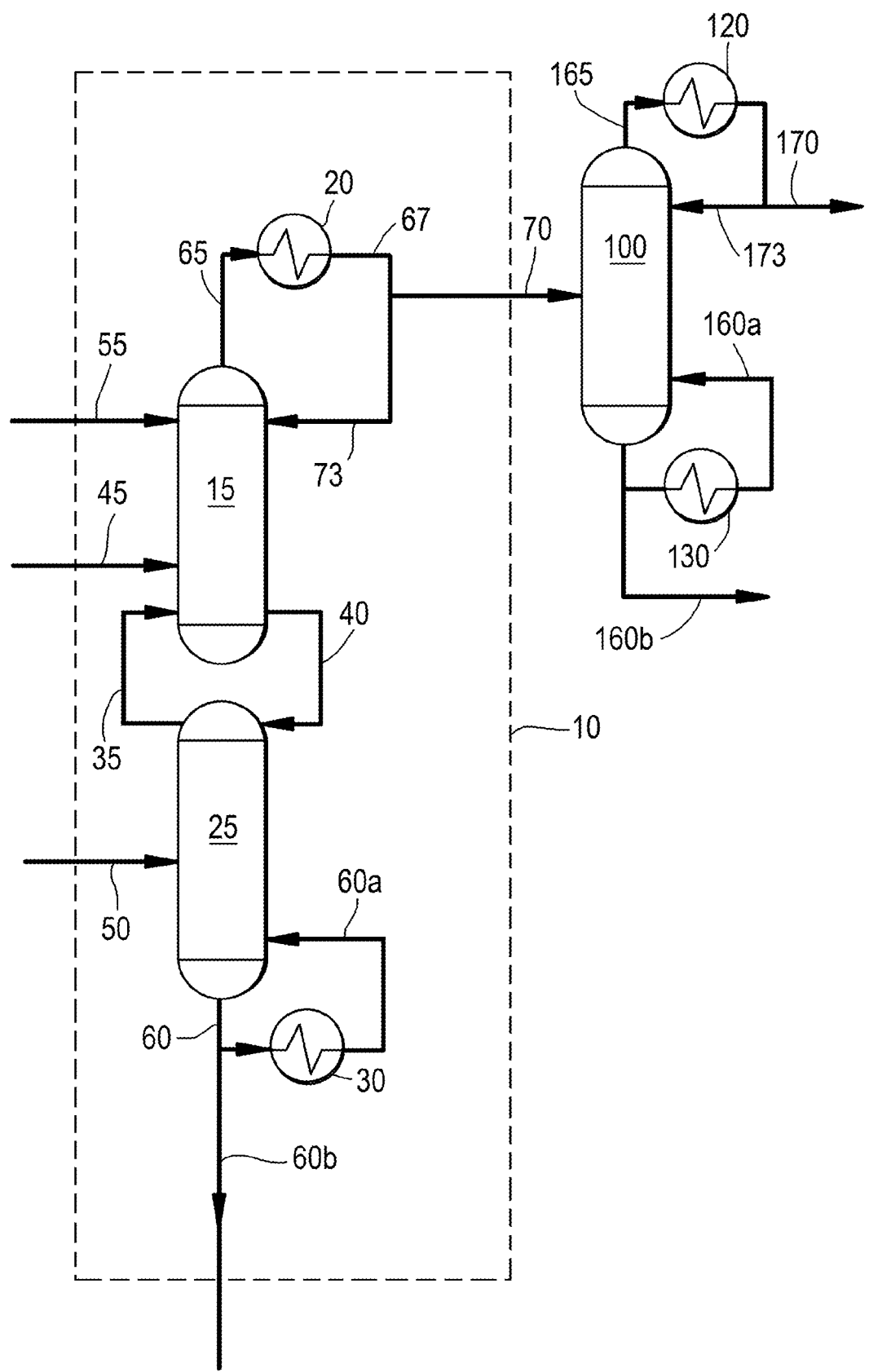

PROCESS FOR REMOVING OXYGENATE FROM AN OLEFIN STREAM

This application claims the benefit of European Application No. 12199686.2 filed Dec. 28, 2012, which is incorporated herein by reference.

FIELD OF THE INVENTION

The present invention relates to a process for removing oxygenate from an olefin stream.

BACKGROUND OF THE INVENTION

Conventionally, ethylene and propylene are produced via steam cracking of paraffinic feedstocks including ethane, propane, naphtha and hydrowax. An alternative route to ethylene and propylene is an oxygenate-to-olefin (OTO) process. Interest in OTO processes for producing ethylene and propylene is growing in view of the increasing availability of natural gas. Methane in the natural gas can be converted into for instance methanol or dimethylether (DME), both of which are suitable feedstocks for an OTO process.

In an OTO process, an oxygenate such as methanol is provided to a reaction zone of a reactor comprising a suitable conversion catalyst whereby the oxygenate is converted to ethylene and propylene. In addition to the desired ethylene and propylene, a substantial part of the oxygenate, such as methanol, is converted to higher hydrocarbons including C4+ olefins and paraffins. The effluent from the reactor comprising the olefins, any unreacted oxygenates such as alcohols or ethers, particularly methanol and dimethylether and other reaction products such as water may then be treated to provide separate component streams. Unreacted oxygenates, in particular methanol, can be separated to a certain extent from the reaction effluent, for instance by contacting with a cooled aqueous stream in a quench zone. In order to increase the ethylene and propylene yield of the process, the C4+ olefins may be recycled to the reaction zone or alternatively further cracked in a dedicated olefin cracking zone to produce further ethylene and propylene.

In patent application WO 03/020678, a process for the removal of dimethylether from an olefinic stream is disclosed. In the process of WO 03/020678, the olefinic stream comprising dimethylether is first separated into a first stream comprising dimethylether and lighter boiling point compounds and a second stream comprising C4+ olefin and higher boiling point hydrocarbons. The stream comprising dimethylether subjected to an extractive distillation using an extraction solvent to remove at least part of the dimethylether. Methanol may for instance be used as a solvent.

A similar process is described in US patent application No. 20090223870, a liquid phase containing hydrocarbons and oxygenates is charged to a separation vessel and separated into a light gaseous fraction and a heavier C4+ fraction. The light gaseous fraction together with a gaseous stream is subjected to an extractive distillation with an extraction solvent, which dissolves the oxygenates, to remove at least part of the oxygenates from the combined gaseous stream. The preferred solvents are methanol or NMP.

Where a gaseous stream is contacted with a liquid solvent, inevitably part of the liquid solvent will evaporate, due to its vapour pressure. As a result the combined gaseous stream is contaminated with the solvent.

Although NMP has the advantage that it has a low vapour pressure, i.e. as much as 100 times lower than methanol, a disadvantage of using NMP is that it is typically not readily available at the process site and thus must be provided externally.

Methanol may be more readily available to use a solvent, however, due to the high vapour pressure of the methanol, the light olefin rich, dimethylether lean overhead vapour stream will comprise substantial amounts of methanol as a contaminant. When methanol is diluted in a non-polar environment, such as the light olefin rich overhead vapour stream, its properties are no longer determined by its ability to form hydrogen bonds with other polar compounds. Rather, the methanol properties are determined based on its molecular weight. Consequently, methanol when diluted in a non-polar environment behaves similar to a C3 hydrocarbon. In the subsequent treatment of the light olefin rich, dimethylether lean overhead vapour stream to isolate ethylene and propylene product streams such diluted methanol will accumulate in the ethylene and propylene product streams. Methanol-contaminated ethylene and propylene is less suitable as a feedstock for preparing olefin derivatives such as polyethylene or polypropylene. Removing, the diluted methanol from the ethylene and propylene product is difficult and energy consuming.

U.S. Pat. No. 7,132,580 discloses a methanol to olefin catalytic conversion process including the selective recovery and recycle of dimethylether and methanol from the effluent stream of the reactor. After the reactor effluent stream is charged to a quench zone, the resulting cooled overhead vapour stream can be compressed. The compressed stream can then be passed to a separation zone to recover a vapour stream which is then passed to a dimethylether absorption zone. The vapour stream is contacted with a dimethylether selective solvent containing methanol at scrubbing conditions effective to produce a liquid solvent bottom stream containing methanol, dimethylether, water and substantial and undesired amounts of ethylene and propylene and a light olefin rich, dimethylether lean overhead vapour stream containing methanol.

The liquid solvent bottom stream further treated to remove a substantial portion of ethylene and propylene contained in the stream. According to U.S. Pat. No. 7,132,580, the use of a dimethylether selective solvent containing methanol in the dimethylether absorption zone necessarily results in a vapour stream that is saturated with methanol at the conditions prevailing at the top of the dimethylether absorption zone. As mentioned above, due to the properties of the diluted methanol in the light olefin rich, dimethylether lean overhead vapour stream, part of the methanol will end up as a contaminant in the ethylene and propylene product streams. Consequently, unless additional steps are taken to rigorously remove methanol from the light olefin rich, dimethylether lean overhead vapour stream, the light olefin product may be contaminated with methanol. The process of U.S. Pat. No. 7,132,580 therefore requires a secondary methanol absorption zone in which the light olefin rich, overhead vapour stream is contacted with an aqueous solvent at scrubbing conditions to remove methanol to produce a dimethylether-lean and methanol-lean overhead vapour product stream comprising ethylene and propylene and a bottom stream containing methanol and aqueous solvent.

Nowowiejski et al. (Nowowiejski et al., An overview of oxygenates in olefins units in relation to corrosion, fouling, product specifications, and safety, Presentation at American Institute of Chemical Engineers 2003 Spring National Meeting, New Orleans, USA, in particular page 16) disclose the risk of methanol breakthrough in a C3 splitter even where the feed to the C3 splitter only contains small amounts of methanol. According to Nowowiejski et al., methanol, entering a C3 splitter producing a polymer grade propylene product, will concentrate in the C3 splitter around the 90 to 95 percent propylene zone in the C3 splitter. If methanol levels in the C3 splitter build up over time, a minor upset or change in operating conditions may result in off-spec methanol contaminated propylene product.

A need exists to provide an improved process for the removal of oxygenates from hydrocarbon streams, in particular hydrocarbons streams containing ethylene and propylene. Preferably, a process that reduces the contamination of the light olefin rich overhead vapour stream with additional methanol.

SUMMARY OF THE INVENTION

It has now been found that the problems encountered with the prior art processes can be solved by utilising a solvent comprising propanol to absorb oxygenates present in an olefin stream. In contrast to the process of U.S. Pat. No. 7,132,580, the use of such a solvent comprising propanol significantly reduces the energy consumption of any secondary solvent absorption zone to remove solvent from the ethylene and or propylene product.

The process of the present invention is particularly suitable to be combined with an oxygenate to olefin (OTO) process, wherein at least part of the effluent of the OTO process is treated to remove oxygenates. An additional advantage is that the spent solvent comprising propanol and absorbed oxygenate from the olefin stream can be used as feed to the OTO process to yield additional light olefins.

Accordingly, the present invention provides a process for removing oxygenate from an olefin stream comprising oxygenate, comprising providing to an oxygenate recovery zone the olefin stream comprising oxygenate and a solvent comprising propanol, treating the olefin stream comprising oxygenate with the solvent, and retrieving from the oxygenate recovery zone at least one oxygenate-depleted olefinic product stream comprising olefin and a spent solvent comprising at least part of the oxygenate.

BRIEF DESCRIPTION OF THE DRAWINGS

FIG. 1 depicts a diagrammatic scheme of one embodiment of a process for removing oxygenate from an olefin stream comprising oxygenate described herein.

While the invention is susceptible to various modifications and alternative forms, specific embodiments thereof are shown by way of example in the drawings and will herein be described in detail. It should be understood that the drawing and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

The process described herein is a process for removing an oxygenate from an olefin stream comprising an oxygenate. The process according to the invention is advantageous because the oxygenate and olefinic product in the olefin stream are treated with a solvent comprising propanol, rather than the dimethylether selective solvent containing methanol described in U.S. Pat. No. 7,132,580. Unlike methanol, the propanol described herein has a low volatility, also in dilute mixtures, such that the propanol described herein is separated from the light hydrocarbons more easily and requiring significantly less energy.

Reference herein to propanol is to 1-propanol (n-propanol), 2-propanol (iso-propanol) or a mixture of two or more thereof.

Reference herein to an olefin stream is to a stream comprising at least olefins.

Reference herein to an olefinic stream is to a stream comprising at least olefins.

Reference herein to a spent solvent is to a solvent that has been in contact with an olefin stream comprising oxygenate. The spent solvent comprises at least part of the oxygenate. The oxygenate herein is oxygenate that was provided to the process as part of the olefin stream comprising oxygenate. The spent solvent will further comprise propanol that was provided to the process as part of the solvent.

Reference herein below to the solvent according to the invention is to a solvent comprising propanol.

In the process described herein, the oxygenate, i.e. the oxygenate that was provided to the process as part of the olefin stream comprising oxygenate, may be a $C_1$ to $C_3$ oxygenate, including alcohols, ethers, aldehydes and ketones, typically one or more methanol, ethanol, n-propanol, isopropanol, tert.-butanol, dimethylether, methylethylether, diethylether, formaldehyde, acetaldehyde, propaldehyde, butaldehyde, acetone, and methylethylketone. In a preferred embodiment of the process according to the invention the olefin stream comprising oxygenate is an olefin stream comprising one or more of methanol, dimethylether, acetaldehyde, and acetone, and the oxygenate-depleted olefinic product is methanol-, dimethylether-, acetaldehyde- and acetone-depleted olefinic product.

The process according to the present invention is particularly preferred for treating olefin stream comprising oxygenates containing no more than 10 wt %, more preferably 5 wt %, even more preferably 1 wt %, still more preferably 0.5 wt %, even still more preferably 0.1 wt % of oxygenate based on the olefin stream comprising oxygenate. Preferably, oxygenate-depleted olefinic product contains less than 100 ppmv, more preferably less than 75 ppmv, even more preferably less than 50 ppmv of oxygenate, based on the hydrocarbons in the olefinic product. In a preferred embodiment, the olefin stream comprising oxygenate is an olefin stream comprising one or more of methanol, dimethylether, acetaldehyde, and acetone, and the methanol-, dimethylether-, acetaldehyde- and acetone-depleted olefinic product contains less than 100 ppmv, more preferably 75 ppmv, even more preferably less than 50 ppmv of one or more of methanol, dimethylether, acetaldehyde, and acetone, based on the hydrocarbons in the methanol-, dimethylether-, acetaldehyde- and acetone-depleted olefinic product, preferably based on the propylene in the methanol-, dimethylether-, acetaldehyde- and acetone-depleted olefinic product.

The olefin stream comprising oxygenate may be any olefin stream comprising oxygenate. Preferably, the olefin stream comprises at least 25 wt % olefin, more preferably 50 wt % olefin, even more preferably at least 60 wt % olefin, and still more preferably at least 70 wt % olefin, based on the olefin stream comprising oxygenates. It is particularly preferred that olefin stream comprising oxygenates comprises at least 25 wt % ethylene and/or propylene, more preferably 50 wt % ethylene and/or propylene, even more preferably at least 60 wt % of ethylene and/or propylene, and still even more preferably at least about 70 wt % of ethylene and/or propylene, based on the olefins in the olefin stream comprising oxygenates. In a preferred embodiment the olefin stream comprising oxygenates comprises at least 50 wt % propylene, even more preferably at least 60 wt % of propylene, and still even more preferably at least about 70 wt % of propylene, based on the olefins in the olefin stream comprising oxygenates.

A preferred olefin stream comprising oxygenates is an olefin stream comprising oxygenates obtained from an oxygenate to olefins process.

As mentioned above the solvent comprises propanol. Preferably, where the solvent comprises propanol, the propanol is n-propanol. Although, iso-propanol has properties comparable to n-propanol and may also be used to absorb oxygenates from olefin streams comprising oxygenate, the present invention preferably uses n-propanol rather than iso-propanol for the reason that the n-propanol has a lesser tendency to freeze in the colder stages of the process.

In a preferred embodiment the solvent comprises propanol and methanol. A solvent comprising both propanol and methanol has the advantage that the properties of both solvents components are combined in the solvent, i.e. the high absorbance of oxygenates by methanol and the lower violability of propanol/methanol mixture. Such a solvent may comprise propanol and methanol in any weight ratio, but preferably in a propanol to methanol weight ratio of 100:1 to 1:100, more preferably 10:1 to 1:10, even more preferably 4:1 to 1:4, still more preferably 4:1 to 1:1.

Where the solvent comprises a combination of propanol and methanol, it is preferably a combination of n-propanol and at least methanol. An additional advantage of the use of a mixture of n-propanol and methanol is that where n-propanol has a freezing point of approximately −126° C. and methanol has a freezing point of approximately −98° C., the mixture may have a freezing point of below that of pure n-propanol. It is believed that this depression of the freezing point of the mixture of n-propanol and methanol compared to pure n-propanol is caused by methanol inhibiting the freezing of n-propanol.

Preferably, the solvent comprises predominantly propanol and methanol as components, more preferably in the range of from 75 to 100 wt % of propanol and methanol, based on the weight of the solvent. Even more preferably, in the range of from 90 to 100 wt %, still more preferably of 97 to 100 wt %, of propanol and methanol, based on the weight of the solvent. The most preferred propanol being n-propanol.

In another embodiment, the solvent comprises predominantly propanol as component, more preferably in the range of from 75 to 100 wt % of propanol, based on the weight of the solvent. Even more preferably, in the range of from 90 to 100 w %, still more preferably of 97 to 100 wt %, of propanol, based on the weight of the solvent.

Highly preferred solvents are solvents comprising n-propanol as the only alcohol and, alternatively, solvents comprising n-propanol and methanol as the only alcohols.

The solvent may however, comprise small amounts of other components, preferably components that have a vapour pressure similar to the alcohol in the solvent under conditions prevailing in the oxygenate recovery zone, such as other C3+ alcohols. Such small amounts of other components may have been introduced for instance by re-using at least part of the spent solvent, optionally after treating the spent solvent to remove absorbed compounds.

Preferably, olefin stream comprising oxygenates is treated with the solvent at a pressure of from 2.5 to 350 bara. More preferred operating pressure ranges are of from 5 to 60 bara, even more preferably 10 to 50 bara. Preferably, the olefins stream comprising oxygenate is treated with the solvent at a temperature in the range of from 0 to 60° C., preferably of from 0 to 50° C.

The olefin stream comprising oxygenates is contacted with the solvent in an oxygenate recovery zone to obtain an oxygenate-depleted product stream comprising olefin and a spent solvent. The oxygenate recovery zone may comprise one or more extraction and/or separation steps. Preferably, at least part of the olefin stream, i.e. the fraction comprising at least the oxygenates, is contacted with the solvent to extract at least part of the oxygenate in the olefin stream. Subsequently, the olefins stream is treated to remove any solvent that was carried over.

The olefin stream comprising oxygenate may be contacted with the solvent according to the invention in any suitable way, including but not limited to liquid-gas contactors, bubble columns, wash columns and extractive distillation columns. In a preferred embodiment, the olefin stream comprising oxygenate is first contacted with the solvent in an extractive distillation process. The extractive distillation process may take place in an extractive distillation vessel or column, which can be of conventional design. Preferably, a packed distillation column is used.

Preferably, the extractive distillation process is carried out at a pressure of from 2.5 to 350 bara. More preferred operating ranges are of from 5 to 60 bara, even more preferably 10 to 50 bara. As the pressure in the extractive distillation vessel increases, the more oxygenate, particularly dimethylether, is removed from the olefin stream.

An extractive distillation process is preferred, for instance over a wash column, as the combination of energy input and solvent addition improves the separation between the components, allowing for an effective removal of even very low concentrations of oxygenate present in the olefin stream comprising oxygenates and reducing the losses of valuable components in the solvent. It may preferably be used for removing of oxygenates from an olefin stream comprising no more than 20 wt % of oxygenates, based on the olefin stream comprising oxygenates. The use of an extractive distillation process to treat the olefin stream comprising oxygenates with the solvent is particularly preferred for treating olefin stream comprising oxygenates containing no more than 10 wt %, more preferably 5 wt %, even more preferably 1 wt %, still more preferably 0.5 wt %, even still more preferably 0.1 wt % of oxygenate based on the olefin stream comprising oxygenate. The use of an extractive distillation process is particularly preferred when the oxygenate is dimethylether.

The extractive distillation process is preferably operated below the boiling point of the solvent and its individual components, and above the boiling point of at least part of the components in olefinic stream comprising oxygenate at the operating conditions prevailing in the distillation column. It is preferred to operate the process such that the formation of two liquid phases in the column is prevented. As the solvent travels through the distillation column, oxygenated contaminants, including DME, are absorbed into the solvent and removed along with the solvent at the bottom of the extractive distillation column. Preferably, the temperature is maintained below a temperature at which propanol or when present methanol start to decompose or vaporise. The extractive distillation process herein may comprise one or more stages and one or more columns, optionally with intermediate reheating or cooling.

Typically, extractive distillation will be operated to allow the C3+ olefins in the olefin stream to be retrieved as a top effluent from the extractive distillation, while the spent solvent comprising at least part of the oxygenate, originally comprised in the olefin stream, is retrieved as a bottom stream. Some of the solvent may however be carried over the top as part of the top effluent. Therefore, preferably the top effluent is further treated to remove at least part of the solvent. Therefore, preferably the process according to the invention includes that in the oxygenate recovery zone the olefin stream comprising oxygenate is first contacted with the solvent and a solvent-comprising olefin stream is obtained. Typically, the solvent-comprising olefin stream is an olefin stream that comprises solvent molecules. Subsequently, the solvent-comprising olefin stream is treated to remove the solvent from the solvent-comprising olefin stream. After removal of the solvent, the oxygenate-depleted olefinic product steam is obtained. It is an advantage of the present invention that where the propanol acts as solvent for unreacted oxygenates in the olefin stream comprising oxygenate, it do not form azeotropic mixtures with light (C2 and C3) hydrocarbons, reducing the complexity of the subsequent separation of the carried over solvent from the olefins to produce the oxygenate-depleted olefinic product stream. It is a particular advantage of the present invention that the propanol that forms the solvent has a boiling temperature that is significantly higher than that of the C2 and particularly C3 olefins in the olefin stream. This distinguishes the process of the present invention from prior art processes using solvents comprising only methanol as the alcohol to extract oxygenates, where the methanol diluted in a hydrocarbon phase has a boiling point similar to C3 hydrocarbons. The higher boiling temperature of the components of the solvent according to the present invention, also when diluted in a hydrocarbon phase, allow for a removal of any carried over solvent at a much lower energy consumption that would have been required when the solvent used was a methanol based solvent.

The extractive distillation may be operated separately or may be combined with one or more other distillation processes. The extractive distillation may be operated in series with one or more de-ethaniser, de-propaniser, de-butaniser or de-pentaniser columns, which respectively separate an olefin stream in a C2– and C3+ fraction, C3– and C4+ fraction, C4– and C5+ fraction, and C5– and C6+ fraction. In one embodiment, the olefin stream comprises propylene and propane next to the oxygenate and the extractive distillation is combined with a propylene/propane separation column, also known as a PP splitter. In another embodiment, where the olefin stream comprises at least C3 and C4 olefins next to the oxygenate, the extractive distillation is combined with a C3–/C4+ separation column, also known as a de-propaniser column.

The spent solvent comprising at least part of the oxygenate may be regenerated by removing at least part to the oxygenate or be used for other purposes.

In a particular embodiment, the olefin stream comprising oxygenate is prepared as part of a reaction effluent stream of an oxygenate to olefins reaction zone wherein an oxygenate feedstock is converted as part of an oxygenate to olefins process. Such a reaction effluent of an oxygenate to olefins reaction zone of an oxygenate to olefins process typically comprises olefins and an amount of oxygenates. These oxygenates may be unreacted oxygenates that were provided to the oxygenate to olefins reaction zone as part of an oxygenate feedstock, however, they may also be reaction products formed inside the oxygenate to olefins reaction zone.

In a further embodiment, where the olefin stream comprising oxygenate is prepared as part of a reaction effluent stream of an oxygenate to olefins reaction zone wherein an oxygenate feedstock is converted as part of an oxygenate to olefins process, and wherein prior to treating the olefin stream comprising oxygenates to remove at least part of the oxygenates, the process may comprise at least the steps of:

v) reacting an oxygenate feedstock in an oxygenate reaction zone in the presence of a catalyst comprising a molecular sieve to produce a reaction effluent stream comprising oxygenate, olefin and water;

vv) separating the reaction effluent stream into a water rich stream comprising oxygenate and water and an olefin stream comprising oxygenate;

Reference herein to an oxygenate feedstock is to a feedstock comprising oxygenates. The oxygenates in the feedstock may be different from the oxygenates in the olefin stream, as explained herein above.

It is a particular advantage of the present process that the liquid solvent itself can be used as a feedstock to an OTO process. Therefore, in a further embodiment, the process further comprises the step of:

(c) passing at least a portion of the spent liquid solvent to the oxygenate to olefins reaction zone together with or a part of the oxygenate feedstock.

The reaction effluent stream obtained from the OTO reaction zone, typically comprises substantial amounts of ethylene and propylene. OTO processes according to the present invention preferably produce a reaction zone effluent comprising at least 25 wt % of ethylene and propylene based on the olefin content in the reaction effluent. In addition to ethylene and propylene, the reaction effluent from the OTO also, preferably comprises C4 and/or C5 tertiary iso-olefins.

When the spent solvent is recycled to the OTO reaction zone together with or as part of the oxygenate feedstock, the propanol may be converted to additional propylene, thereby further increasing the propylene yield of the OTO process.

An advantage of using the solvent according to the present invention is that the propanol has a lower vapour pressure than methanol in particular diluted form, more particular when present in diluted from in a non-polar hydrocarbon environment. As a result, the propanol is not transported to the olefinic vapour phase to the extent methanol is, i.e. under equal conditions, however even more importantly, any the presents of propanol in addition to methanol in the solvent reduces the amount of methanol that is carried over to the olefinic vapour phase. In addition, propanol that is transported to the olefinic vapour phase may removed from the olefinic vapour phase at significantly less energy cost than methanol and without having to accept accumulation of solvent in the ethylene and or propylene fractions in the final product slate. Rather, the propanol is preferably directed to the C4+ fractions.

As mentioned herein above, the process according to the invention is particularly useful to be combined with an oxygenate-to-olefin process or OTO process. In an OTO process oxygenates, preferably oxygenates such as methanol and dimethylether are converted over a molecular sieve catalyst to at least ethylene and propylene. The ethylene and propylene are retrieved from the OTO process as part of an olefin stream, which typically also comprises C4+ olefins and paraffins and oxygenates. The oxygenates may be unreacted feed components or may have been formed during the OTO process.

OTO process are well known in the art and have for instance been described in WO A 2006/020083. Processes integrating the production of oxygenates from synthesis gas and their conversion to light olefins are described in US20070203380A1 and US20070155999A1.

The oxygenate used in an oxygenate feedstock provided to the OTO process is preferably an oxygenate which comprises at least one oxygen-bonded alkyl group. The alkyl group preferably is a C1-C5 alkyl group. Preferably, the oxygenate is methanol or dimethylether, or a mixture thereof.

A diluent, such as water or steam, may also be provided to the OTO process together with or as part of the oxygenate feedstock. Preferably, in addition to the oxygenate and diluent, an olefinic co-feed is provided along with and/or as part of the oxygenate feedstock. The olefinic co-feed preferably comprises C4+ olefins i.e. C4 and higher olefins, more preferably C4 and C5 olefins. Preferably, at least part of the olefinic co-feed, during normal operation, is formed by a recycle stream of a C4+ hydrocarbon fraction from the OTO reaction effluent, i.e. the olefin stream obtained from the OTO process. In order to maximize production of ethylene and propylene, it is desirable to maximize the recycle of C4 olefins in the effluent of the OTO process as these olefins are converted to further ethylene and propylene. Where reference is made to an OTO process, this is to process that produces significant amounts of ethylene and propylene by converting at least part of the feedstock. Preferably, olefin steam, as obtained from the OTO process, comprises at least 50 wt % of ethylene and/or propylene, based on the hydrocarbon content of the olefin steam.

Catalysts suitable for converting the oxygenate feedstock comprise one or more molecular sieves. Such molecular sieve-comprising catalysts typically also include binder materials, matrix material and optionally fillers. Suitable matrix materials include clays, such as kaolin. Suitable binder materials include silica, alumina, silica-alumina, titania and zirconia, wherein silica is preferred due to its low acidity.

Molecular sieves preferably have a molecular framework of one, preferably two or more corner-sharing tetrahedral units, more preferably, two or more [SiO4], [AlO4] and/or [PO4] tetrahedral units. These silicon, aluminum and/or phosphorus based molecular sieves and metal containing silicon, aluminum and/or phosphorus based molecular sieves have been described in detail in numerous publications including for example, U.S. Pat. No. 4,567,029. In a preferred embodiment, the molecular sieves have 8-, 10- or 12-ring structures and an average pore size in the range of from about 3 Å to 15 Å. Suitable molecular sieves are silicoaluminophosphates (SAPO), such as SAPO-17, -18, 34, -35, -44, but also SAPO-5, -8, -11, -20, -31, -36, 37, -40, -41, -42, -47 and –56; aluminophosphates (AlPO) and metal substituted (silico) aluminophosphates (MeAlPO), wherein the Me in MeAlPO refers to a substituted metal atom, including metal selected from one of Group IA, IIA, IB, IIIB, IVB, VB, VIB, VIIB, VIIIB and Lanthanides of the Periodic Table of Elements. Preferably Me is selected from one of the group consisting of Co, Cr, Cu, Fe, Ga, Ge, Mg, Mn, Ni, Sn, Ti, Zn and Zr.

Alternatively, the conversion of the oxygenate feedstock may be accomplished by the use of an aluminosilicate-comprising catalyst, in particular a zeolite-comprising catalyst. Suitable catalysts include those containing a zeolite of the ZSM group, in particular of the MFI type, such as ZSM-5, the MTT type, such as ZSM-23, the TON type, such as ZSM-22, the MEL type, such as ZSM-11, and the FER type. Other suitable zeolites are for example zeolites of the STF-type, such as SSZ-35, the SFF type, such as SSZ-44 and the EU-2 type, such as ZSM-48.

Aluminosilicate-comprising catalyst, and in particular zeolite-comprising catalyst are preferred when an olefinic co-feed is fed to the oxygenate conversion zone together with oxygenate, for increased production of ethylene and propylene.

Preferred catalysts for OTO processes comprise SAPO, MEL and/or MFI type molecular sieves, whereby the latter two are zeolite molecular sieves. More preferred catalyst comprise SAPO-34, ZSM-11 and/or ZSM-5 type molecular sieves. A preferred MFI-type zeolite for the OTO catalyst has a silica-to-alumina ratio, SAR, of at least 60, preferably at least 80. More preferred MFI-type zeolite has a silica-to-alumina ratio, SAR, in the range of 60 to 150, preferably in the range of 80 to 100.

The catalyst may further comprise phosphorus as such or in a compound, i.e. phosphorus other than any phosphorus included in the framework of the molecular sieve. It is preferred that a MEL or MFI-type zeolite comprising catalyst additionally comprises phosphorus.

The reaction conditions of the oxygenate conversion, include a reaction temperature of 350 to 1000° C., preferably from 350 to 750° C., more preferably 450 to 700° C., even more preferably 500 to 650° C.; and a pressure from 0.1 kPa (1 mbara) to 5 MPa (50 bara), preferably from 100 kPa (1 bara) to 1.5 MPa (15 bara).

Preferably, the oxygenate feedstock is preheated to a temperature in the range of from 200 to 550° C., more preferably 250 to 500° C. prior to contacting with the molecular sieve-comprising catalyst.

The olefin stream exiting the OTO process may be suitably treated to remove oxygenates from such stream by the process according to the present invention. Preferably, prior to passing the olefin stream to the oxygenate recovery zone the olefin stream is treated to remove water and heavy (C7+) hydrocarbons. The olefin stream may, prior to passing the olefin stream to the oxygenate recovery zone, further be treated to remove low boiling fractions such as methane, hydrogen and carbon oxides.

The olefin stream, preferably after water has been removed, can be passed to a compressor, in which the pressure of the stream is increased. In one embodiment of the invention, the treatment of the olefin stream comprising oxygenates with the solvent occurs immediately after quenching and preferably compressing of the olefin steam obtained from the OTO process. In another embodiment, the olefin stream comprising oxygenates is optionally treated to remove a C2– hydrocarbon fraction and optionally a C4+ fraction, typically in two or more separate columns. Preferably, at least an olefin stream comprising C3 hydrocarbon fraction is treated with the solvent, as most of the oxygenates will be part of the C3 hydrocarbon fraction.

The spent solvent comprising the oxygenate can, at least in part, be passed to the OTO process. This could, for instance, be done as a part of an olefinic co-feed stream.

Where herein it is mentioned that the olefin stream comprising oxygenate is obtained from the effluent of an oxygenate to olefins process, such a olefin stream may also be obtained from the combined effluent of a oxygenate to olefin process and a steam cracking process.

EXAMPLE

The present invention is illustrated by the following non-limiting calculated example.

The extractive distillation removal of DME from a DME-containing hydrocarbon stream was modelled for several solvents using Aspen V7.3 with an in-house version of the PSRK-UNIFAC property method to describe the thermodynamic behaviour of the system.

The modelled set-up includes a de-propaniser consisting of a high-pressure column section with a condenser and a low-pressure column section with a reboiler. The solvent is added to the high pressure column section of the de-propaniser. The distillate retrieved from the high-pressure column is treated in a separate solvent removal column. The extractive distillation set-up as used in the model calculation is shown in FIG. 1.

In FIG. 1, there is shown de-propaniser 10 consisting of high-pressure column section 15 with condenser 20 and low-pressure column section 25 with reboiler 30. The top stream of low-pressure column section 25 is provided, while being condensed and pressurised (not shown), to high-pressure column section 15 via means 35, while the liquid bottom steam of high-pressure column section 15 flows to low-pressure column section 25 via means 40. A first feed stream 45 is provided to high-pressure column section 15. This first feed stream may for instance be obtained from a de-ethaniser column used to separate the C2– fraction from an olefin stream comprising oxygenate for example an olefin stream obtained from a OTO process. A second feed stream 50 is provided to low-pressure column section 25. This second feed stream may for instance be obtained from the compression section where an olefin stream comprising oxygenate, for example obtained from a OTO process, is compressed in one or more stages of a compressor train or the compression section. In the final stages of the compression of the olefin stream, a liquid hydrocarbon stream condenses out from the olefin stream. This condensate is subsequently stripped in a condensate stripper to remove any entrained C3 and lighter hydrocarbons. These C3 and lighter hydrocarbons are provided to de-propaniser 10.

Solvent stream 55 is provided close to the top of high-pressure section 15 of depropaniser 10.

Of liquid fraction 60 exiting the bottom of low-pressure column section 25, part 60a is passed to reboiler 30 and returned to low-pressure column section 25. Another part 60b is removed and further treated (not shown) to for instance recover the C4+ hydrocarbons and the solvent. Vapor fraction 65 exiting the top of high-pressure column section 15, is passed to condenser 20. Condensed stream 67 is split, with condensed stream 70 being passed to separate solvent removal column 100, while condensed stream 73 is recycled to high-pressure column section 15.

Solvent removal column 100 is equipped with condenser 120 and reboiler 130. Of liquid fraction 160 exiting the bottom of solvent removal column 100, part 160a is passed to reboiler 130 and returned to solvent removal column 100. Another part 160b is removed and further treated (not shown) to for instance recover the solvent. Vapor fraction 165 exiting the top of solvent removal column 100, is passed to condenser 120. Condensed stream 170 is retrieved as oxygenate-depleted olefinic product, while part of condensed stream 170 is recycled as stream 173 to solvent removal column 100.

In the model calculations reboiler duty of reboiler 130 and distillate flow rate (condensed stream 70) were varied to achieve a fixed C4 loss, as part of the distillate of de-propaniser 10, of 0.0005 kmol/h and a fixed recovery of 95 mol % of propylene in the distillate of de-propaniser 10, based on the propylene in the total feed to de-propaniser 10. These values are typically aimed for in normal depropaniser operation.

The feed to de-propaniser 10, i.e. first feed stream 45 and second feed stream 50, is shown in Table 1.

TABLE 1

|   |   | First feed stream (45) | Second feed stream (50) |
|---|---|---|---|
| Temperature | ° C. | 70 | 74 |
| Pressure | barg | 23.2 | 15.6 |
| Mass flow | kg/h | 69915 | 44596 |
| Mole flow | kmol/s | 0.43 | 0.23 |
| Component |  | mol % | mol % |
| C2— |  | 0.07% | 0.02% |
| total C3 |  | 78% | 33% |

TABLE 1-continued

| mole fraction C3= in total C3 | 0.94 | 0.89 |
|---|---|---|
| total C4 | 20% | 45% |
| total C5 | 2% | 15% |
| total C6 | 0% | 4% |
| DME | 0.08% | 0.07% |

The described model is used to model DME extraction using no solvent (not according to the invention), a solvent consisting of methanol (not according to the invention), a solvent consisting of n-propanol, and a solvent consisting of a 75/25 weight mixture of n-propanol and methanol, whereby the aim is to reduce the DME concentration in the condensed stream (70) exiting the de-propaniser (10) to approximately 50 ppmv. Table 2 shows the composition of the condensed stream (70) and the solvent removal column (100) reboiler (130) duty required to remove the carried over solvent from the final oxygenate-depleted olefinic product. As can be seen from Table 2, with the exception of the case wherein no solvent is present, it is possible to reach a 50 ppm (mole) DME concentration in the condensed stream (70) exiting the de-propaniser. The required methanol flow rates to de-propaniser (10) are lower than that of n-propanol, however due to the high tendency of the methanol to carry over into the condensed stream (70) exiting the de-propaniser, the condensed stream (70) becomes rich in methanol, which is difficult to remove due to its similar boiling point to propylene at low concentrations. The solvent content in condensed stream (70) is similar for each of the three calculated examples, i.e. methanol, propanol and the mixture of propanol and methanol, when calculated on a mole basis. The solvent content, on a mole basis, of condensed steam (70), however, is the lowest when using the propanol/methanol mixture followed by the use of propanol. As mentioned before, methanol is difficult to remove from the propylene in the condensed stream 70. This is seen when calculating the reboiler (130) duty required to remove the solvent from condensed stream (70) in the solvent removal column (100) to obtained the desired oxygenate-depleted olefin product. As can be seen from Table 2, the use of propanol solvent decreases the required reboiler (130) duty in the solvent removal column (100) by as much as 59% for a similar DME removal efficiency. The reduction in reboiler duty is attributed to the higher boiling temperatures of n-propanol even at low concentration in non-polar hydrocarbon environment.

Using a mixture of propanol and methanol reduces the carryover of solvent to condensed stream (70), while at the same time reducing the required reboiler (130) duty compared to the use of a methanol solvent. Where the solvent mixture comprises of 25 wt % of methanol, the solvent fraction that was carried over in to condensed stream (70) comprises less than 25 wt % of methanol, reducing the fraction of difficult to remove methanol. Moreover, as mentioned herein above, the where the use of n-propanol requires a higher solvent flow rate compared to methanol, adding methanol to n-propanol to obtain a solvent comprising a mixture of n-propanol and methanol significantly reduces the required solvent flow rate in de-propanizer (10), making effective use of the enhanced DME absorption ability of the methanol. Due to the combined effects of the lowered solvent flow rate in de-propanizer (10), the lower solvent carry over into solvent recovery column (100) and the reduced reboiler (130) duty, the use of a solvent comprising both n-propanol and methanol is beneficial to the process according to the present invention.

TABLE 2

| Condensed stream (70) | | no solvent* | MeOH* | n-PrOH | nPrOH/MeOH 75/25 on weight |
|---|---|---|---|---|---|
| DME# | ppmv | 313 | 44 | 50 | 50 |
| Solvent content# | wt % | 0 | 6 | 10.5 | n-PrOH: 7.3 MeOH: 1.6 |
| reboiler (130) duty | MW | 0 | 13.9 | 5.7 | 9.9 |

*not according to the invention
based C3 content in condensed stream 70

What is claimed is:

1. A process for removing oxygenate from an olefin stream comprising oxygenate, comprising providing to an oxygenate recovery zone the olefin stream comprising oxygenate and a solvent comprising a mixture of methanol and propanol in a weight ratio of in the range of 4:1 to 1:1, treating the olefin stream comprising oxygenate with the solvent, and retrieving from the oxygenate recovery zone at least one oxygenate-depleted olefinic product stream comprising olefin and a spent solvent comprising at least part of the oxygenate.

2. The process of claim 1, wherein the oxygenate is one or more of methanol, dimethylether, acetaldehyde and acetone.

3. The process of claim 1, wherein the olefin stream comprising oxygenate is treated with the oxygenate absorption stream in an extractive distillation process.

4. The process of claim 1, wherein in the oxygenate recovery zone the olefin stream comprising oxygenate is first contacted with the solvent and a solvent comprising olefin steam is obtained and subsequently the solvent comprising olefin steam is treated to remove the solvent from the solvent comprising olefin steam and the oxygenate-depleted olefinic product steam is obtained.

5. The process of claim 1, wherein the olefin stream comprising oxygenate is prepared as part of a reaction effluent stream of an oxygenate to olefins reaction zone, wherein an oxygenate feedstock is converted as part of an oxygenate to olefins process by reacting the oxygenate feedstock in an oxygenate reaction zone in the presence of a catalyst comprising a molecular sieve which converts oxygenates to olefins.

6. The process of claim 1, wherein prior to treating the olefin stream comprising oxygenate to remove oxygenate, the process comprises at least the steps of:
   v) reacting an oxygenate feedstock in an oxygenate reaction zone in the presence of a catalyst comprising a molecular sieve to produce a reaction effluent stream comprising oxygenate, olefin and water; and
   vv) separating the reaction effluent stream into a water rich stream comprising oxygenate and water and an olefin stream comprising oxygenate.

7. The process of claim 5, further comprising step of:
   c) passing at least a portion of the spent liquid solvent to the oxygenate to olefin reaction zone together with or as part of the oxygenate feedstock.

8. The process of claim 1, wherein the olefin stream comprising oxygenate is compressed prior to being provided to the oxygenate recovery zone.

* * * * *